(12) United States Patent
Mujwid

(10) Patent No.: US 7,559,943 B2
(45) Date of Patent: Jul. 14, 2009

(54) SPINAL FIXATION DEVICE WITH INTERNAL DRIVE STRUCTURE

(75) Inventor: James R. Mujwid, Crystal, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 430 days.

(21) Appl. No.: 10/865,674

(22) Filed: Jun. 9, 2004

(65) Prior Publication Data

US 2005/0277925 A1 Dec. 15, 2005

(51) Int. Cl.
*A61B 17/70* (2006.01)

(52) U.S. Cl. ........................ 606/266; 606/270

(58) Field of Classification Search ................. 606/246, 606/250–253, 257, 264–270, 279
See application file for complete search history.

(56) References Cited

U.S. PATENT DOCUMENTS

| | | | |
|---|---|---|---|
| 5,129,388 A | 7/1992 | Vignaud et al. | |
| 5,443,467 A | 8/1995 | Biedermann et al. | |
| 5,476,464 A | 12/1995 | Metz-Stavenhagen | |
| 5,628,740 A | 5/1997 | Mullane | |
| 5,672,176 A | 9/1997 | Biedermann et al. | |
| 5,728,097 A | 3/1998 | Mathews | |
| 5,733,286 A | 3/1998 | Errico et al. | |
| 5,735,850 A | 4/1998 | Baumgartner et al. | |
| 5,879,350 A | 3/1999 | Sherman et al. | |
| 5,882,350 A | 3/1999 | Ralph et al. | |
| 6,050,997 A | 4/2000 | Mullane | |
| 6,074,391 A | 6/2000 | Metz-Stavenhagen et al. | |
| 6,113,601 A | 9/2000 | Tatar | |
| 6,248,105 B1 | 6/2001 | Schlapfer et al. | |
| 6,280,442 B1 | 8/2001 | Barker et al. | |
| 6,287,309 B1 | 9/2001 | Baccelli et al. | |
| 6,355,040 B1 | 3/2002 | Richelsoph et al. | |
| 6,371,957 B1 | 4/2002 | Amrein et al. | |
| 6,488,681 B2 | 12/2002 | Martin et al. | |
| 6,540,748 B2 * | 4/2003 | Lombardo | 606/61 |
| 6,716,214 B1 * | 4/2004 | Jackson | 606/61 |
| 2005/0038432 A1 * | 2/2005 | Shaolian et al. | 606/61 |

FOREIGN PATENT DOCUMENTS

DE 2246274 A * 3/1974

OTHER PUBLICATIONS

Centerpulse Spine-Tech Inc. product specification sheet for Dynalok™ (New), © 2003, 2 pages.
Centerpulse Spine-Tech Inc. product specification sheet for Dynalok™ (Old), © 2003, 2 pages.

(Continued)

*Primary Examiner*—William H. Matthews
(74) *Attorney, Agent, or Firm*—Crompton, Seager & Tufte, LLC.

(57) ABSTRACT

A bone screw arrangement including a retainer and an anchor. The retainer includes a first receiving region configured for receipt of a connecting rod, and a second receiving region configured for receipt of the anchor. The second receiving region includes an upper socket and a lower socket. The arrangement includes an interface that transfers torque applied to the retainer, to the anchor for securing the anchor to a bone element.

33 Claims, 12 Drawing Sheets

OTHER PUBLICATIONS

Centerpulse Spine-Tech Inc. product specification sheet for Monarch™, © 2003, 2 pages.

Centerpulse Spine-Tech Inc. product specification sheet for Steffee™ Plate, © 2003, 2 pages.

DuPuy AcroMed™ catalog for Monarch™ Spine System, no date provided, cover and p. 6.

Medicrea® catalog for PASS MED™ Polyaxial Spine System, © Jan. 2002.

* cited by examiner

SPINAL FIXATION DEVICE WITH INTERNAL DRIVE STRUCTURE

TECHNICAL FIELD

This disclosure relates generally to devices, and associated methods, for stabilizing spinal alignment. More particularly, this disclosure relates to a medical implant, such as a bone screw device configured to receive a connecting rod, and associated methods.

BACKGROUND

The human spinal column is prone to diseases or disorders that produce disruption of the normal alignment of the spine. Frequently, treatment of spinal disorders involves spinal stabilization, for example, by immobilization of the affected vertebral joint(s). One spinal stabilization technique includes a surgical process wherein implants are attached to the spinal vertebrae and connected with spinal rods. In particular, a combination of bone screw arrangements and connecting rods are used to provide a stabilizing construct secured to the spinal vertebrae for the purpose of stabilizing and/or adjusting spinal alignment.

Conventional bone screw arrangements generally include a bone screw and a yoke member for securing a rod in relation to the bone screw arrangement. Some arrangements further include a separate locking piece that operates in conjunction with the yoke member and bone screw to lock the bone screw in an angular position. The yoke member typically includes an upper pocket for receiving the rod. The separate locking piece is typically positioned within the yoke at a location below the upper pocket. The bone screw often includes a spherical head that seats within the separate locking piece. Prior to final fixation of the rod, the angle of the bone screw can be adjusted relative to the yoke. A securing piece (e.g. a threaded plug or ring) is secured to the yoke to lock the rod within the yoke, and to lock the bone screw at a particular angular position relative to the yoke via the locking piece.

The bone screw typically includes internal drive structure, such as an internal hex socket, formed in the head of the bone screw. The hex socket is adapted for receiving a wrench for use in driving the bone screw into a bone element. In use, the head of the bone screw is seated within the bottom region of the yoke with the hex socket facing upwardly so as to be accessible through the yoke. To fasten the bone screw to a bone element, a wrench or other tool is inserted downwardly through the yoke and into the internal hex of the bone screw. The bone screw is then driven into the bone element by applying torque to the internal hex. After the bone screw has been driven into the bone element, the rod is positioned within the yoke, and the securing member is mounted to the yoke to lock the rod within the yoke, and to lock the bone screw at a particular angular position relative to the yoke via the locking piece.

The size of a bone screw arrangement is important for minimizing the invasiveness of the surgical procedure. Yet, size is also important for maintaining the structural integrity of the arrangement when applying torque and other forces to the components of the bone screw arrangement. Often, in attempting to provide a less invasive arrangement by reducing the size of the arrangement's components, the structural integrity of the arrangement is jeopardized. For example, a common problem of smaller sized arrangements having internal hex sockets is that the internal hex socket strips or experiences excessive wear.

In the alternative, larger sized arrangements that can accommodate the greater torque loading are more invasive and create a greater risk to the patient. In addition, a larger internal hex formed in the bone screw head of the arrangement has limited accessibility. For example, the size of the internal hex can be no greater than the size of the opening provided in the yoke through which a drive tool, such as an allen wrench, is inserted. If the internal hex is maximized to accommodate as much torque loading as possible, problems arise in aligning the allen wrench with the internal hex. In other words, as the size of the internal hex increases, the more difficult it becomes to align a correspondingly sized tool with the internal hex due to a lesser amount of space and lesser tolerance for misalignment.

Moreover, when the bone screw is at certain angles relative to the yoke, the hex socket can be difficult to access. This is typically problematic in procedures involving the removal of a particular bone screw assembly, but the screw has been locked within the yoke at an angle where the hex socket cannot be readily accessed through the yoke.

In general, improvement has been sought with respect to such devices and arrangements, generally to better accommodate: ease of use, reliability, manufacture, and assembly; and to minimize invasiveness.

SUMMARY

One aspect of the present disclosure relates to a bone screw arrangement for use with a connecting rod. The arrangement includes a retainer and an anchor. The retainer has a first receiving region configured to receive a connecting rod, and a second receiving region having internal drive structure. The anchor is positioned within the second receiving region of the retainer. The anchor has external drive structure that interfaces with the internal drive structure of the retainer.

Another aspect of the present disclosure relates to a bone screw arrangement having a yoke for receiving a connecting rod and an anchor. The anchor has a head that mounts at least partially within the yoke. The head includes external drive structure that fits within an internal drive socket defined by the yoke.

Still another aspect of the present disclosure relates to a method of using a bone screw arrangement, the arrangement including a retainer and an anchor. The method includes applying torque to the retainer to drive the anchor into an object, pivoting the retainer relative to the anchor, and securing the anchor and the retainer in a fixed position relative to one another.

Yet another aspect of the present disclosure relates to a method of manufacturing a bone screw arrangement. The method includes forming external drive structure on an anchor and forming internal drive structure on a retainer, the internal drive structure corresponding to the external drive structure of the anchor. The method also includes forming a first receiving region within the retainer, the first receiving region being configured to receive a connecting rod, and coupling the anchor to the retainer.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

DETAILED DESCRIPTION

Reference will now be made in detail to various features of the present disclosure that are illustrated in the accompanying drawings. Wherever possible, the same reference numbers will be used throughout the drawings to refer to the same or like parts.

Figure 1:
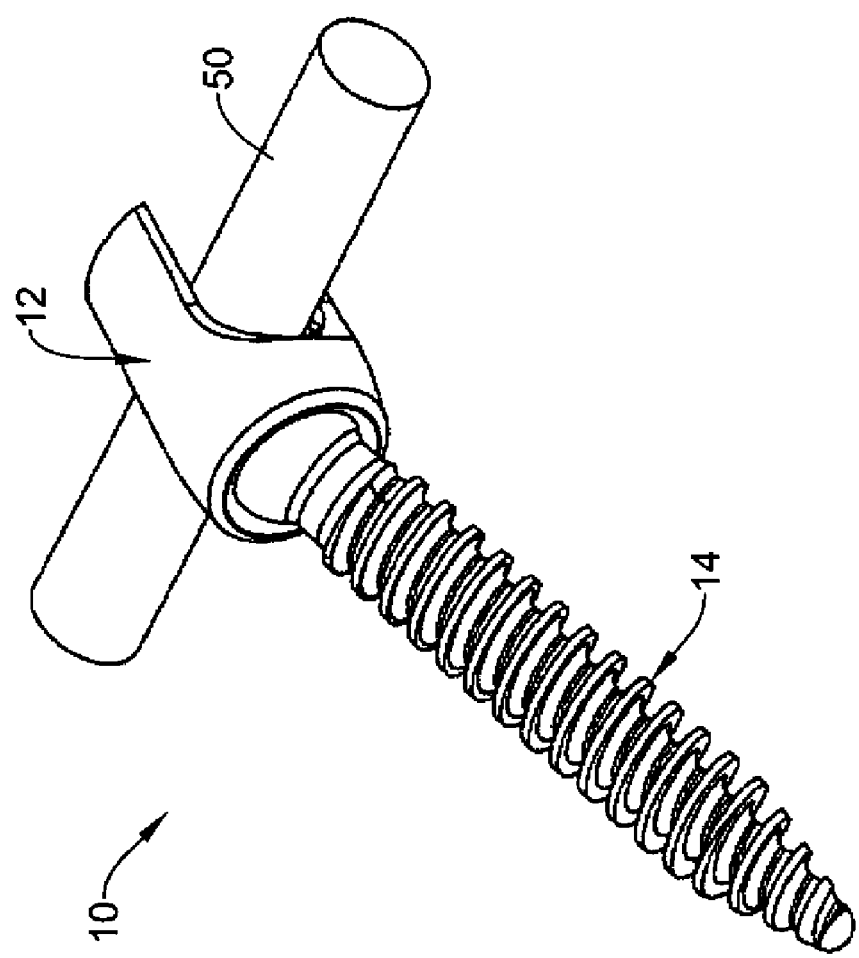
FIG. 1 is a perspective view of one embodiment of a bone screw arrangement, according to the principles of the present disclosure.
Figure 2:
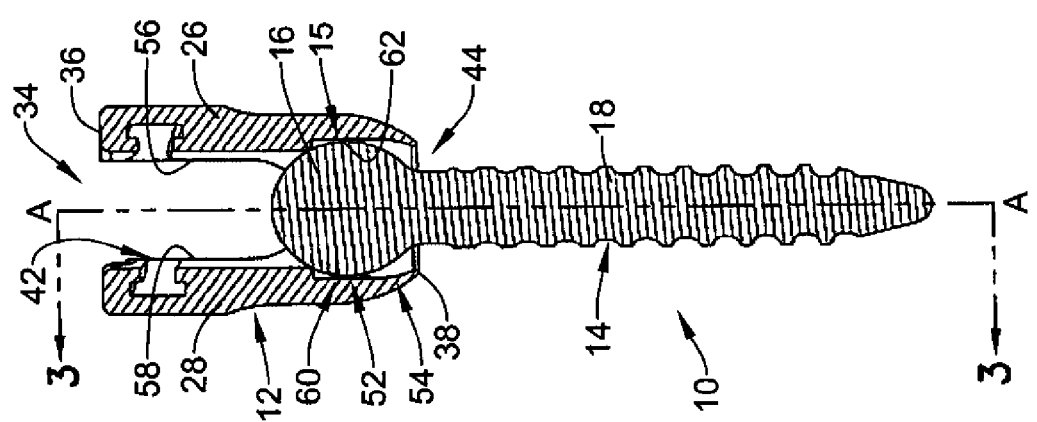
FIG. 2 is a cross-sectional view of the bone screw arrangement of FIG. 1, shown during a surgical driving step, and taken along line 2-2 shown in FIG. 3.
Figure 3:
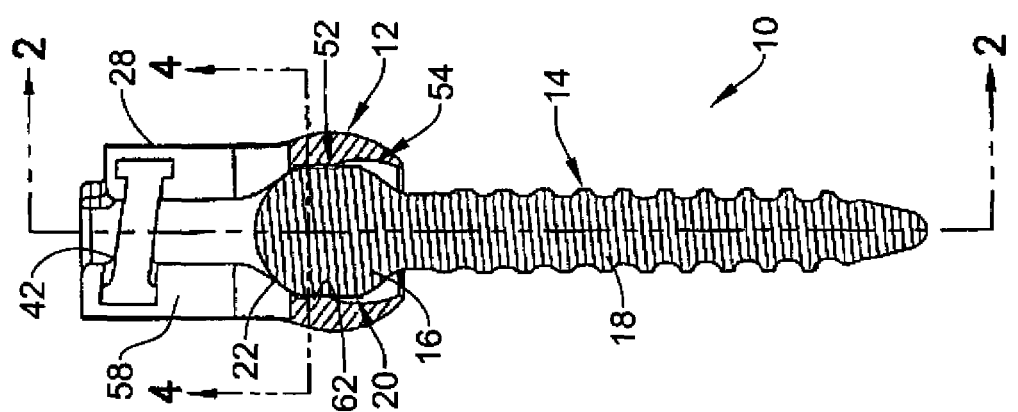
FIG. 3 is another cross-sectional view of the bone screw arrangement of FIG. 2, taken along line 3-3.
Figure 4:
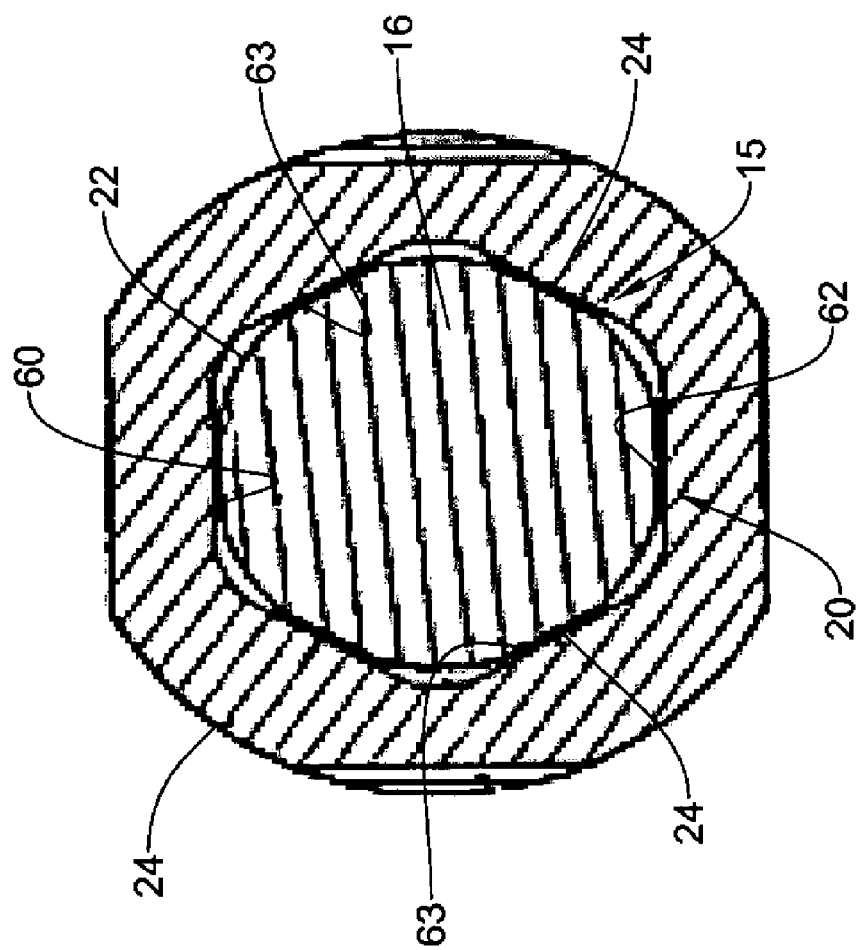
FIG. 4 is a top cross-sectional view of the bone screw arrangement of FIG. 3, taken along line 4-4.
Figure 5:
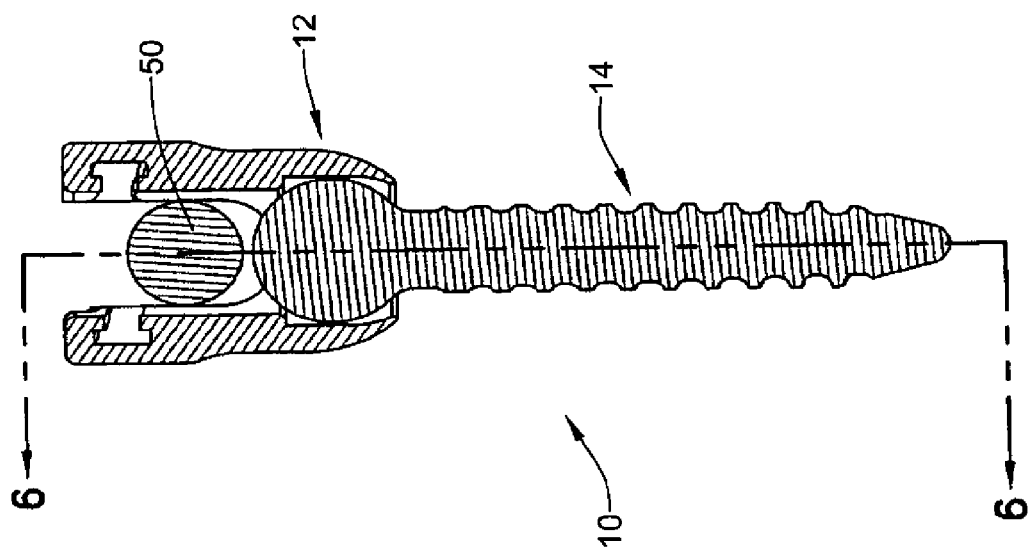
FIG. 5 is a cross-sectional view of the bone screw arrangement of FIG. 1, shown during transition from the driving step to a surgical locking step, and taken along line 5-5 shown in FIG. 6.
Figure 6:
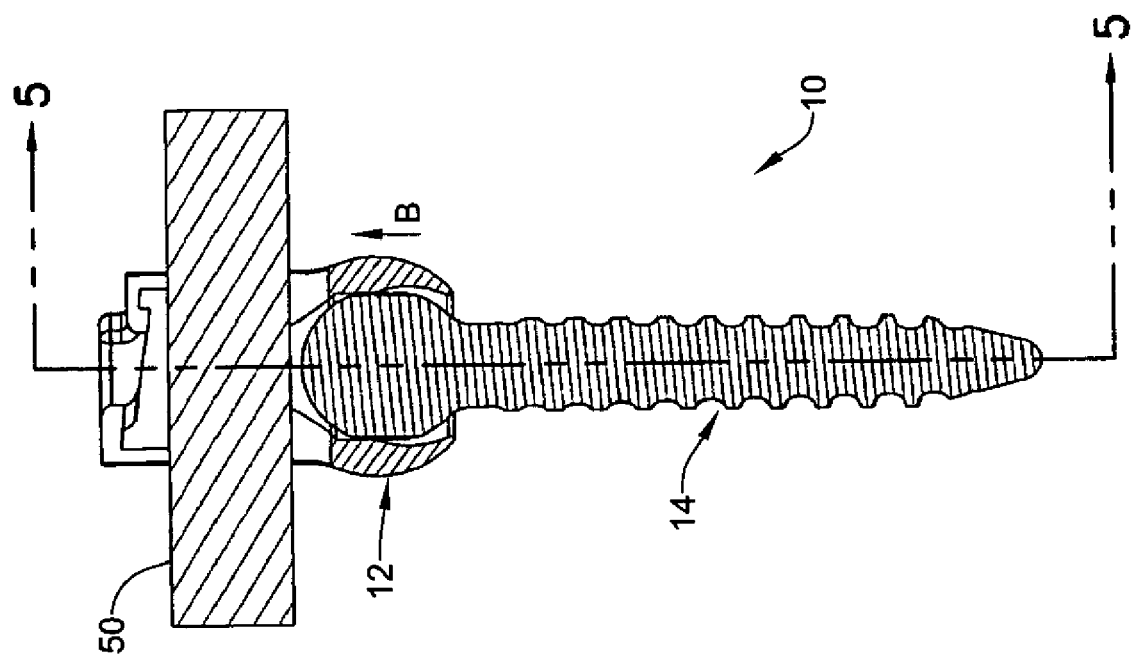
FIG. 6 is another cross-sectional view of the bone screw arrangement of FIG. 5, taken along line 6-6.
Figure 7:
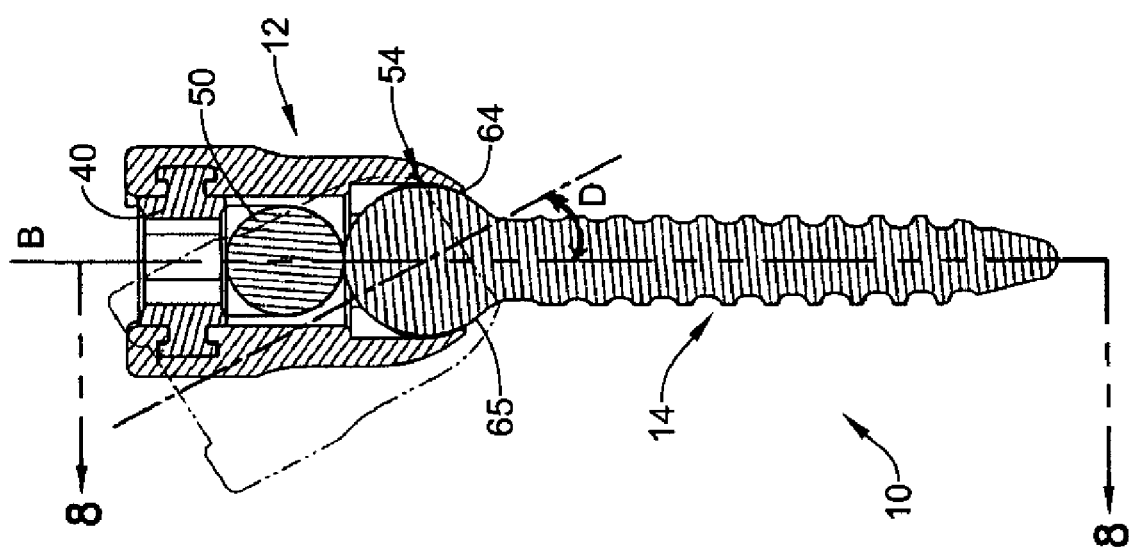
FIG. 7 is a cross-sectional view of the bone screw arrangement of FIG. 1, shown during a surgical locking step, and taken along line 7-7 shown in FIG. 8.
Figure 8:
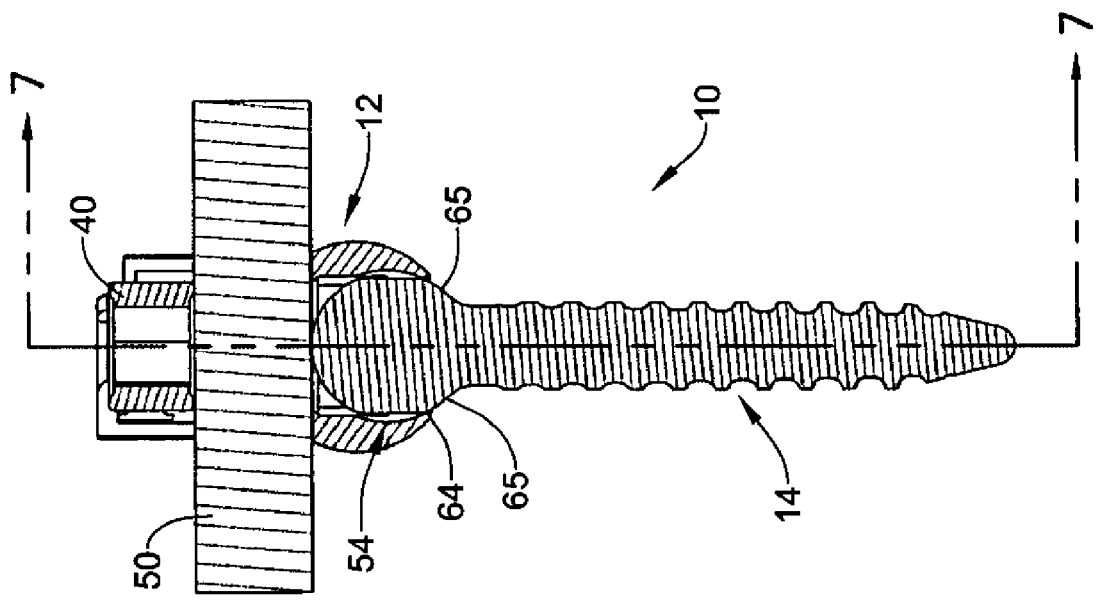
FIG. 8 is another cross-sectional view of the bone screw arrangement of FIG. 7, taken along line 8-8.

FIG. 1 illustrates a bone screw arrangement 10 in accord with the principles of the present disclosure. The bone screw arrangement 10 is designed for use with a connecting rod 50 in spinal stabilization surgeries. The bone screw arrangement 10 generally includes a yoke or retainer 12 and an anchor 14 (also known as bone screw or pedicle screw). The bone screw arrangement 10 includes a drive interface 15 (FIG. 4) between the retainer 12 and the anchor 14 that transfers torque applied to the retainer, to the anchor to secure the arrangement to an object, such as a bone element. FIGS. 2-4 illustrate the arrangement 10 during a surgical step of driving the anchor into a bone element; FIGS. 7 and 8 illustrate the arrangement 10 during a surgical step of locking the anchor 14 relative to the retainer 12; and FIGS. 5 and 6 illustrate the arrangement 10 in transition from the driving step to the locking step.

Referring to FIGS. 2-4, the bone screw arrangement 10 is illustrated in a configuration for use in driving the anchor 14 into a bone element during a surgical procedure. In general, the anchor 14 has a head 16 and a shank 18. As shown in FIG. 3, the head 16 of the anchor 14 is a solid construction; that is, the head 16 does not include an internal bore, internal hex, or other internal configuration formed within the head of the anchor. Rather, the head 16 includes external drive structure 20 formed on an outer surface 22 of the head 16. In the illustrated embodiment, the drive structure 20 includes external flats 24 formed on the outer surface 22 of the head 16. Any number of flats 24 can be used. In this particular arrangement, six flats 24 are provided.

The retainer 12 of the present disclosure includes a retainer body 32 having a first receiving region 34 (e.g., a connecting rod pocket) located adjacent to a first end 36 of the retainer and a second receiving region 44 (e.g., an anchor head pocket) located adjacent to a second end 38 of the retainer. The first receiving region 34 is configured to receive the connecting rod 50. The second receiving region 44 is configured to receive the head 16 of the anchor 14.

The second receiving region 44 of the retainer body 32 includes an upper socket region 52 and a lower socket region 54. The upper socket region 52, as shown in FIG. 4, is constructed to correspond to the external drive structure 20 of the anchor head 16. In particular, the upper socket region 52 is a drive socket that includes internal drive structure 60. The internal drive structure 60 mates with the external drive structure 20 of the head 16 of the anchor. The internal drive structure 60 and the external drive structure 20 define the drive interface 15 of the bone screw arrangement 10. In the illustrated embodiment, the internal drive structure 60 is a polygonal-like structure 62 having internal flats 63 that corresponds to the external flats 24 formed on the outer surface 22 of the anchor head 16.

During the step of driving the anchor 14 into a bone element, the anchor 14 is positioned within the upper socket region 52 by aligning the external flats 24 on the head 16 of the anchor 14 with the internal flats 63 of the retainer 12. In this position, the anchor 14 is fixed relative to the retainer 12. That is, the anchor 14 is prevented from rotating or pivoting relative to the retainer 12. Also in this position, as shown in FIGS. 2 and 3, the anchor 14 is generally aligned with a longitudinal axis A-A of the retainer 12.

When the anchor head 16 is seated within the upper socket region 52, the anchor 14 can be driven into its desired location. As can be understood, the anchor 14 and the retainer 12 rotate in unison with one another during the driving step of the surgical procedure.

Figure 11:
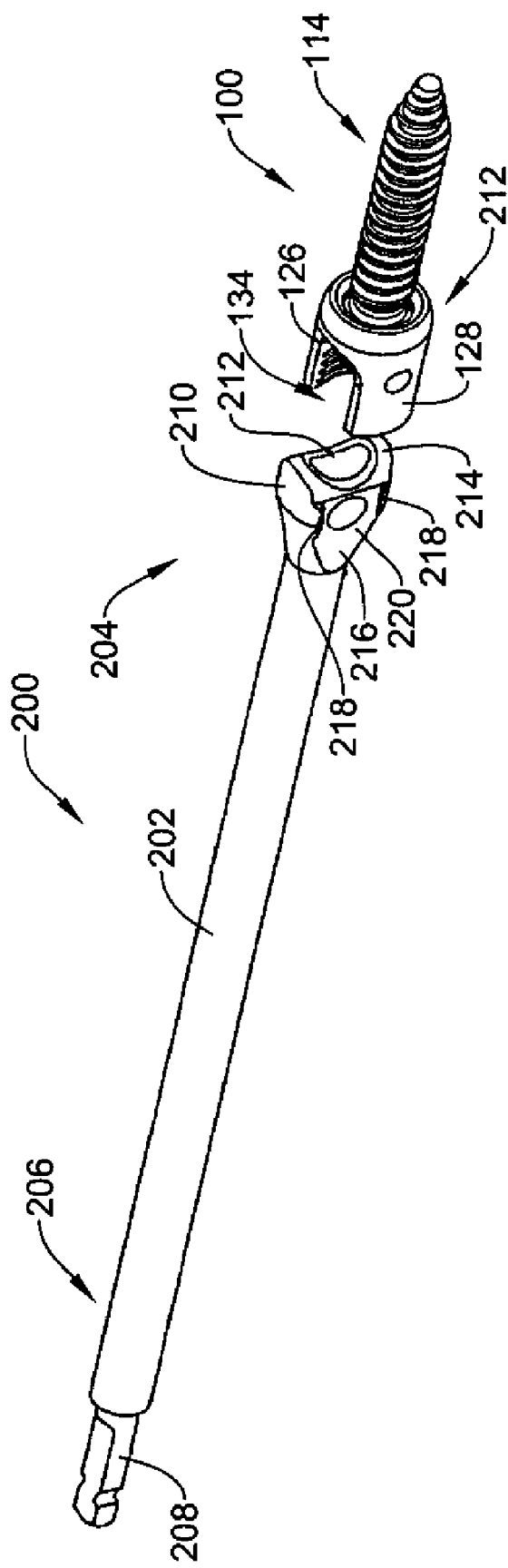
FIG. 11 is a perspective view of a driving tool that can be used with a bone screw arrangement, according to the principles of the present disclosure, the driving tool is shown disengaged from the bone screw arrangement.
Figure 12:
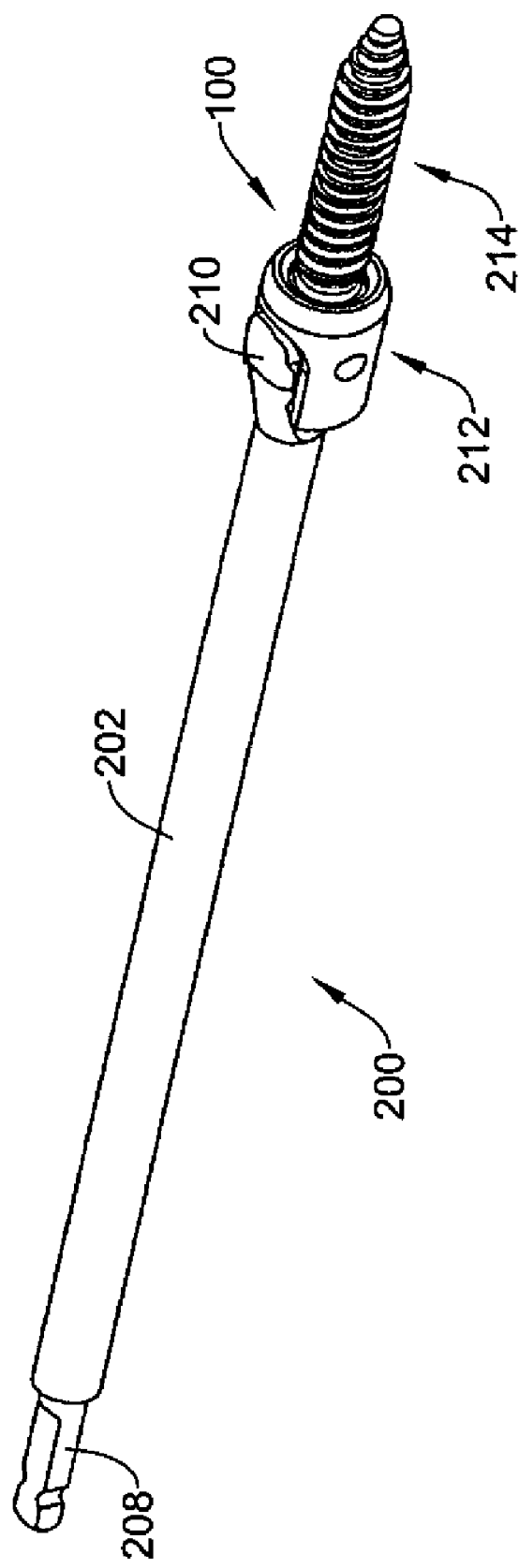
FIG. 12 is a perspective view of the driving tool of FIG. 11, shown engaged with the bone screw arrangement.

Referring now to FIGS. 11 and 12, to drive the anchor 14 into its desired location, a tool 200 couples to or engages with the first receiving region 34 (134) of the retainer 12 (212). The tool 200 is used to apply torque to the retainer 12, which in turn transfers the torque through the drive interface 15 (i.e. the internal drive structure 60 of the upper socket region 52 and the external drive structure 20 of the anchor head 16) of the bone screw arrangement 10 to drive the anchor 14 into a bone element. The drive interface 15 of the arrangement 10 between the retainer 12 and the anchor 14 permits the anchor 14 to be driven by applying torque to the retainer 12, rather than by applying torque directly to the anchor head 16.

Because torque is applied to the retainer 12 instead of the anchor 14, a more robust and easy to use interface is provided. As previously described, in conventional arrangements, the interface is typically an internal hex formed in the anchor head. The internal hex is often undersized due to size restrictions of the anchor head. The undersized interface had a tendency to strip or become excessively worn when torque was applied to drive the anchor into a bone element. In addition, the conventional internal hex is also difficult to access, and sometimes even hidden from view when a corresponding tool is inserted into the yoke.

The present arrangement 10 eliminates the difficulty in maneuvering a tool to access an internal hex formed within a small exposed portion of an anchor head. The present arrangement 10 also provides a larger interface between the tool and the retainer 12 (versus the tool and the anchor) to enhance the structural integrity of the interface. In addition, because an internal hex is no longer formed in the head 16 of the anchor 14, the head 16 of the anchor 14, and the retainer 12 can be downsized to minimize invasiveness of the arrangement 10.

Referring again to FIGS. 11 and 12, one embodiment of the tool 200 is illustrated. The tool 200 generally includes a shaft 202 having a first end 204 and a second end 206. The second end 206 includes attachment structure 208. The attachment structure 208 is configured to couple to a handle (not shown) or other drive devices for applying toque to the bone screw arrangement 10 (100).

The tool 200 also includes drive structure 210 located at the first end 204 of the tool 200. The drive structure 210 is sized and configured to engage the first receiving region 34 (134) of the retainer 12 (112). In the illustrated embodiment, the drive structure has a convex forward face 214 and side faces 216 (only one side face shown). A recess 212 is formed on a forward face 214 of the drive structure. The recess 212 is shaped to correspond to the head 16 of the anchor 14, and the convex forward face 214 is shaped to correspond to the concave configuration of the first receiving region 34. The recess 212 and the convex forward face 214 permit the drive structure 210 to seat completely within the first receiving region 34.

Notches 220 formed on the side faces 216 define lips 218 on opposite edges of the side faces 216. The lips 218 help to guide and align the tool 200 in relation to the retainer 12 when inserting the drive structure 210 into the first receiving region 34. The notches 220 of the side faces 216 provide clearance for threaded features formed within the first receiving region 34. In the illustrated embodiment, the notches 220 are sized and configured to correspond to first and second arms 26 (126), 28 (128) (FIG. 2) of the retainer 12.

Referring now to FIGS. 5 and 6, once the anchor 14 is secured to the bone element, the tool 200 is removed from the first receiving region 34 of the retainer 12. A release force is applied to the anchor 14 and the retainer 12, for example, by pulling the retainer 12 in a direction away from the anchor 14 (represented by arrow B in FIG. 6). At this point, a connecting rod 50 may or may not be positioned within the first receiving region 34. If a connecting rod 50 is at least partially secured within the first receiving region, a user may pull on the connecting rod to apply the release force. The release force releases or disengages the head 16 of the anchor from the internal drive structure 60 of the upper socket region 52. The head 16 of the anchor 14 is then positioned within the lower socket region 54 of the second receiving region 44 of the retainer 12.

Referring now to FIGS. 7 and 8, the lower socket region 54 is a spherical construction that permits the retainer 12 to pivot or swivel (shown in dashed lines) relative to a longitudinal axis B-B of the anchor 14. The retainer 12 may be pivoted to assist in placing a connecting rod 50 within the first receiving region 34 of the retainer 12 after the anchor 14 has been driven into the desired location. Preferably, the bone screw arrangement 10 is configured to permit the retainer 12 to pivot relative to the longitudinal axis B-B of the anchor 14 at an angle D of between 0 and 50 degrees, in any direction; more preferably between 0 and 30 degrees, in any direction. In other words, the retainer 12 and the anchor 14 preferably have a universal-type range of motion from one angled position to an opposite angled position of between 0 and 100 degrees; more preferably between 0 and 60 degrees.

Referring still to FIGS. 7 and 8, the connecting rod 50 is positioned within the first receiving region 34 of the retainer 12. At this point in some surgical procedures, the anchor 14 may still be positioned within the upper socket region 52, depending upon whether or not the retainer 12 needed to be pivoted for placement of the connecting rod 50. To secure the connecting rod 50 within the first receiving region 34 and to lock the anchor 14 in a fixed position relative to the retainer 12, a securing member 40 is coupled to the retainer 12.

In the illustrated embodiment of FIGS. 2-8, the securing member 40 is a T-thread member that couples to the first and second arms 26, 28 that extend outward from a main body portion 30 of the retainer 12. The first and second arms 26, 28 at least partially define the first receiving region 34 of the retainer 12. Each of the first and second arms 26, 28 includes slotted structure 42 that corresponds to the T-thread member 40. In the illustrated embodiment, the slotted structure 42 is formed on opposing inner surfaces 56, 58 of the arms 26, 28. The T-thread member 40 is a corresponding T-thread setscrew that mates with the internal threads 42 of the arms 26, 28.

The securing member 40 is driven into the retainer 12 to seat the connecting rod 50 within the first receiving region 34 of the retainer 12. As the securing member 40 is turned relative to the retainer 12, the securing member 40 rides downwardly along the slotted structure 42 and contacts the connecting rod 50 to force the connecting rod 50 against the head 16 of the anchor 14. If the anchor 14 has not been previously disengaged from the internal drive structure 60 of the upper socket region 52, the connecting rod 50 in turn urges the anchor 14 to move from the upper socket region 52 to the lower socket region 54.

To lock all of the components (i.e. the retainer 12, the anchor 14, and the connecting rod 50) relative to one another, the user continues to drive the securing member 40 downwardly within the first receiving region 34 until the securing member 40 is tightened and fully seated. As the securing member 40 is being tightened, the connecting rod 50 contacts and is forced against the head 16 of the anchor 14. The connecting rod 50 loads the anchor 14 such that the head 16 of the anchor 14 is wedged against a bottom edge 64 of the lower socket region 54. Each of the retainer 12, the anchor 14, and the connecting rod 50 are now locked in a fixed position relative to one another.

Still referring to FIGS. 7 and 8, the anchor 14 of the present disclosure is configured to lock in any desired fixed position (i.e. at any desired angle D) relative to the retainer 12 with equal locking force regardless of the relative angle D between the retainer 12 and the anchor 14. In particular, the head 16 of the anchor 14 has a lower spherical portion 65 that contacts the bottom edge 64 of the lower socket region 54. The lower spherical portion 65 is located below the flats 24 formed on the head 16 and provides full surface contact between the head 16 of the anchor 14 and the bottom edge 64 of the retainer 12. The full surface contact provides a locking force that is generally equal regardless of the selected relative angle of the retainer 12 and the anchor 14.

Figure 9:
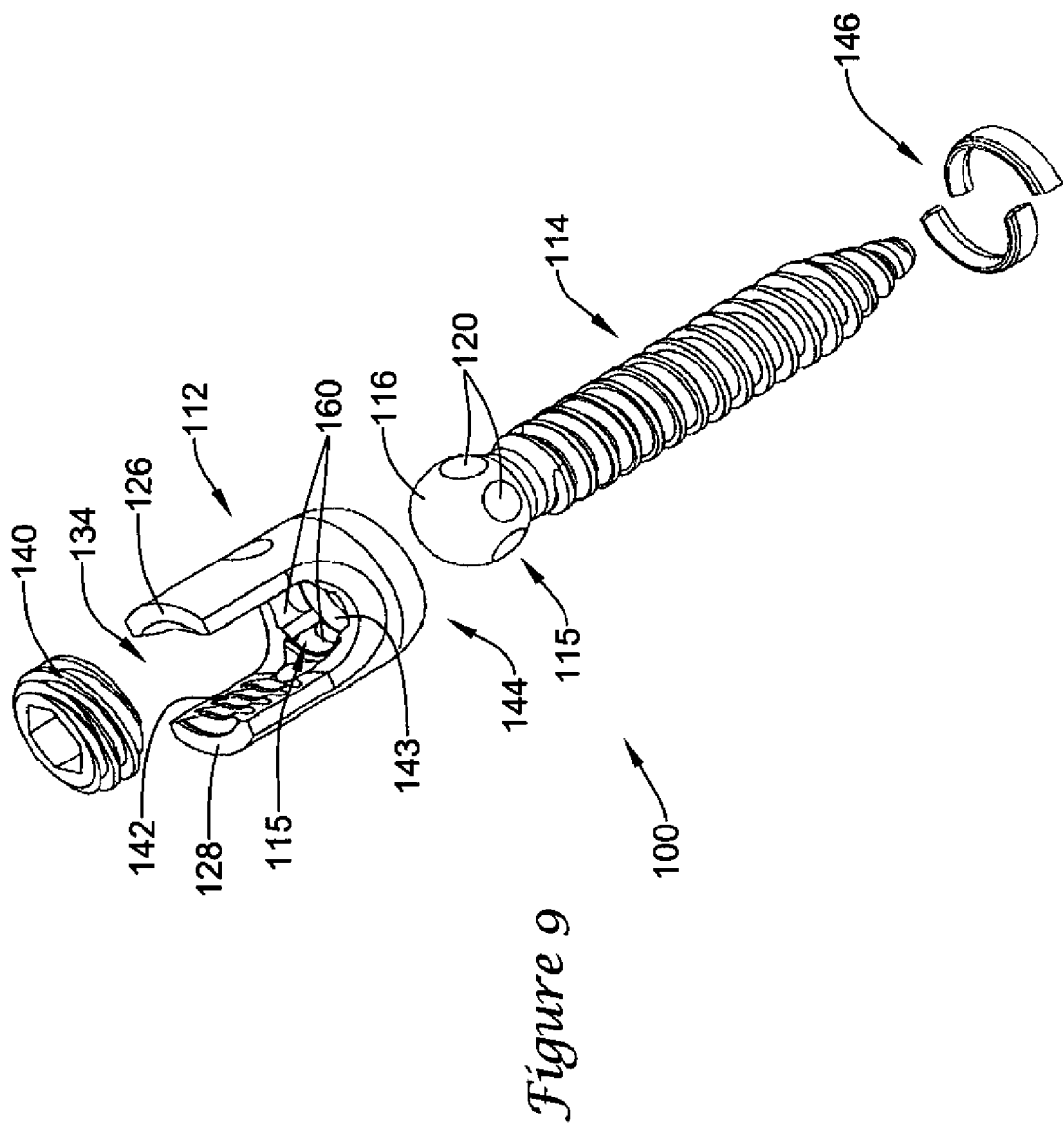
FIG. 9 is an exploded, perspective view of another embodiment of a bone screw arrangement, according to the principles of the present disclosure.
Figure 10:
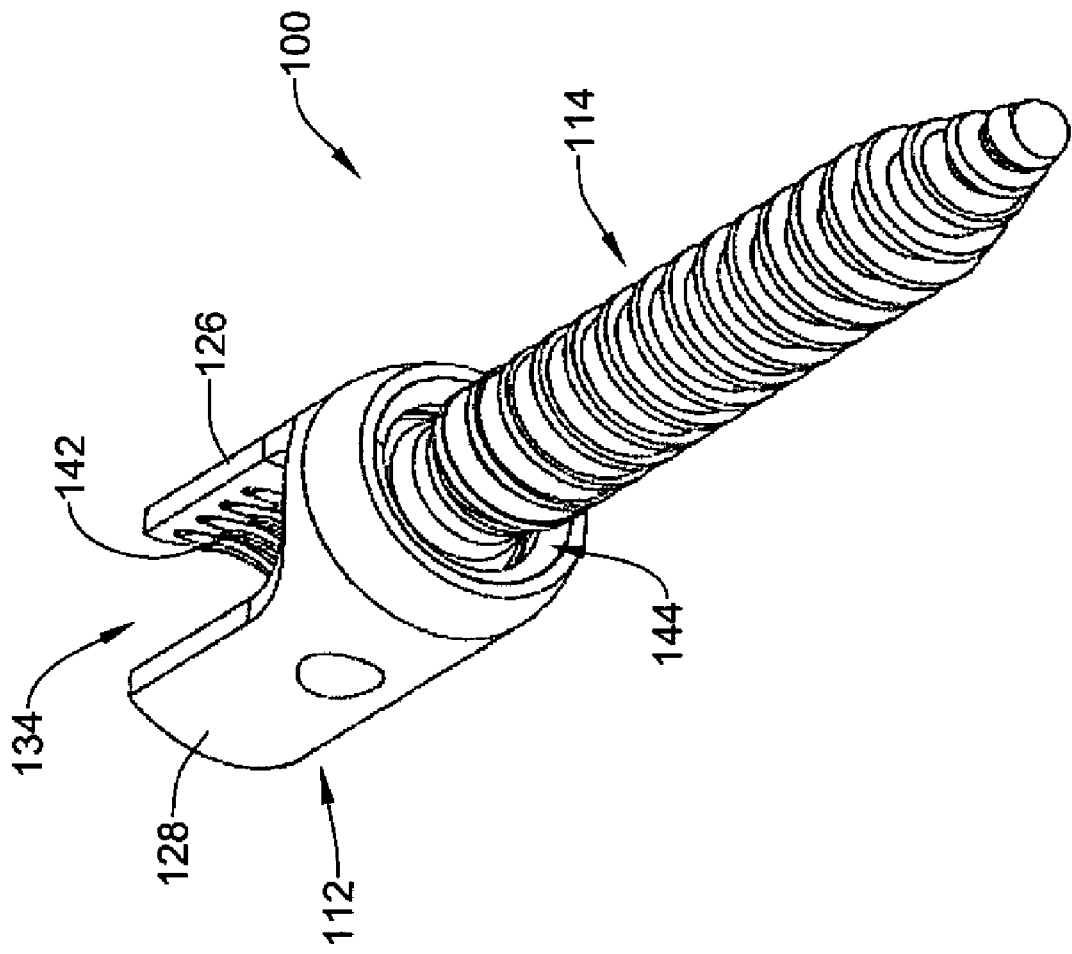
FIG. 10 is an assembled perspective view of the bone screw arrangement of FIG. 9.

Referring now to FIGS. 9 and 10, a second embodiment of a bone screw arrangement 100 is illustrated. Similar to the previous arrangement, the second arrangement 100 generally includes a retainer 112, an anchor 114 and a drive interface 115 that transfers torque applied to the retainer, to the anchor to secure the arrangement to an object, such as a bone element.

The retainer 112 includes a first receiving region 134 and a second receiving region 144. The second receiving region 144 includes an upper socket region and a lower socket region (not shown) similar to the previous embodiment. Internal drive structure 160 formed in the retainer 112 and external drive structure 120 formed on the head 116 of the anchor 114 define the drive interface 115 of the bone screw arrangement 10.

In the second embodiment, the arrangement is assembled by first positioning the head 116 of the anchor 114 within the second receiving region 144 of the retainer 112. The tip of anchor 114 can either be dropped in through the first receiving region 134 and through the second receiving region 144, or, the head 116 of the anchor 114 can be inserted into the second receiving region 144. A retaining ring 146 is then positioned within a groove 143 formed at the bottom of the second receiving region 144. The retaining ring 146 can be then be welded, bonded, or otherwise permanently or temporarily secured to the retainer 112 to capture the head 116 of the anchor 114 within the second receiving region 144.

In contrast, in the first arrangement, the anchor 14 can only be dropped in through the first receiving region 34 as the bottom edge 64 of the second receiving region is not sized to permit the head 16 of the anchor 14 to be inserted directly into the second receiving region 44.

Still referring to the second arrangement 100 of FIGS. 9 and 10, to secure a connecting rod 50 within the first receiving region 134, and to lock the anchor 114 in a fixed position relative to the retainer 112, a securing member 140 is coupled to the retainer 112.

The illustrated securing member 140 of the second arrangement 100 is a threaded member that couples to first and second arms 126, 128 of the retainer 112. Each of the first and second arms 126, 128 includes threads 142 that correspond to the threaded member 140. In the illustrated embodiment, the threads 142 are internal threads formed on inner surfaces of the arms 126, 128. The threaded member 140 is a corresponding setscrew or plug that mates with the internal threads 142 of the arms 126, 128.

Similar to the previous embodiment, to lock all of the components (i.e. the retainer 112, the anchor 114, and the connecting rod 50) relative to one another, the user drives the securing member 140 within the first receiving region 134 until the securing member is tightened and fully seated. As the securing member 140 is being tightened, the connecting rod 50 is forced against the head 116 of the anchor 114. The connecting rod 50 loads the anchor 114 such that the head 116 of the anchor 114 is wedged against the retaining ring 146. Each of the retainer 112, the anchor 114, and the connecting rod 50 are now in a fixed position relative to one another.

In each of the embodiments of the present disclosure, torque is applied to the retainer 12, 112 instead of the anchor 14, 114 to provide a more robust and easy to use interface. The disclosed interface reduces wear and the occurrence of stripping, as the interface is located at the external surface of the anchor head and therefore larger in size than conventional internal hex designs. Also, the problem of accessing an internal hex of a bone screw is eliminated. Rather, the tool 200 illustrated in FIGS. 11 and 12 simply and easily engages the first receiving region 34, 134 to drive the anchor into a bone element.

Because an internal hex is no longer formed in the head 16, 116 of the anchor 14, 114, the head of the anchor, and the retainer 112 can be downsized to minimize invasiveness of the arrangement 10, 100. In addition, each of the arrangements of the present disclosure eliminates the need for a separate locking piece to secure all of the components in a fixed position relative to one another. Buy eliminating the need for a separate locking piece, the overall size and profile of the bone screw arrangement 10, 100 is further reduced to minimize the invasiveness of the surgical stabilization procedures. In alternative embodiments, however, the disclosed principles of the internal drive structure of the retainer and the external drive structure of the anchor can be incorporated in arrangements that include a separate locking piece.

The above specification provides a complete description of the present invention. Since many embodiments of the invention can be made without departing from the spirit and scope of the invention, certain aspects of the invention reside in the claims hereinafter appended.

What is claimed is:

1. A bone screw arrangement for use with a connecting rod, the arrangement comprising:
   a) a retainer including a first receiving region configured to receive a connecting rod, and a second receiving region having internal drive structure comprising a plurality of internal flat surfaces; and
   b) an anchor including a head and a shank extending from the head, the head of the anchor positioned within the second receiving region of the retainer, the head of the anchor including external drive structure comprising a plurality of external flat surfaces that interface with the internal flat surfaces of the internal drive structure of the retainer such that torque can be transferred between the internal drive structure of the retainer and the external drive structure of the anchor;
   wherein the retainer is selectively pivotable relative to the anchor between a plurality of angular orientations; and
   wherein internal flat surfaces of the internal drive structure contact external flat surfaces of the external drive structure to transfer torque applied to the retainer to the anchor.

2. The arrangement of claim 1, wherein the first receiving region is adapted to engage a tool for applying torque to the retainer, whereby the applied torque is transferred between the internal drive structure of the retainer and the external drive structure of the anchor.

3. The arrangement of claim 2 wherein the first receiving region is configured to receive the tool for applying torque to the retainer.

4. The arrangement of claim 1, wherein the anchor head has a solid construction.

5. The arrangement of claim 4, wherein the external flat surfaces are arranged around an outer peripheral surface of the anchor head.

6. The arrangement of claim 1, wherein the anchor is positionable in a first position at which the external drive structure of the anchor is engaged with the internal drive structure of the retainer, and a second position at which the external drive structure of the anchor is disengaged from the internal drive structure of the retainer.

7. The arrangement of claim 6, wherein the anchor and the retainer are in a fixed position relative to one another when the anchor is in the first position.

8. The bone screw arrangement of claim 6
   wherein the anchor and the retainer are permitted to pivot relative to one another when the anchor is in the second position.

9. The bone screw arrangement of claim 6
   wherein the second receiving region includes upper socket and lower socket regions, the internal drive structure being located within the upper socket region.

10. The arrangement of claim 9, wherein the upper socket region is configured to prevent the anchor and the retainer from pivoting relative to one another.

11. The arrangement of claim 10, wherein the upper socket region is configured to prevent the anchor and the retainer from rotating relative to one another.

12. The arrangement of claim 9, wherein the lower socket region has a spherical construction that permits the anchor and the retainer to pivot relative to one another.

13. The arrangement of claim 1, further including a securing member that locks the retainer, the anchor, and a connecting rod positioned within the first receiving region in a fixed position relative to one another.

14. The arrangement of claim 1, wherein the second receiving region includes upper socket and lower socket regions, the anchor being selectively positionable in both of the upper and lower socket regions.

15. The arrangement of claim 14, wherein the internal drive structure is located within the upper socket region of the retainer.

16. The arrangement of claim 14, wherein the upper socket region of the second receiving region prevents the anchor from pivoting relative to the retainer when the anchor is positioned in the upper socket region.

17. The arrangement of claim 14, wherein the upper socket region of the second receiving region prevents the anchor from rotating relative to the retainer when the anchor is positioned in the upper socket region.

18. The arrangement of claim 14, wherein the anchor is selectively pivotable when the anchor is positioned in the lower socket region of the second receiving region.

19. The arrangement of claim 1, wherein the anchor includes a head having a spherical portion configured to provide full surface contact between the head of the anchor and the retainer when the head of the anchor is positioned within a lower socket of the second receiving region.

20. The arrangement of claim 1, wherein the torque can be transferred between the internal drive structure of the retainer and the external drive structure of the anchor in the absence of the connecting rod in the first receiving region.

21. A bone screw arrangement for use with a connecting rod, the arrangement comprising:
   a) a yoke including a first arm, a second arm and a rod receiving region defined between the first arm and the second arm for receiving a connecting rod, the yoke defining an internal drive socket including a plurality of internal flat surfaces;
   b) an anchor having a head that mounts at least partially within the yoke, the head having an external drive structure including a plurality of external flat surfaces arranged around a periphery of the head, at least a portion of the head is positioned within the internal drive socket such that the plurality of external flat surfaces of the external drive structure of the head of the anchor interface with the plurality of internal flat surfaces of the internal drive socket of the yoke such that torque can be transferred from the yoke to the anchor; and
   c) a fastener positioned between and engaged with the first arm and the second arm of the yoke for securing a connecting rod in the rod receiving region of the yoke;
   wherein internal flat surfaces of the internal drive socket contact external flat surfaces of the external drive structure to transfer torque applied to the yoke to the anchor.

22. The arrangement of claim 21, wherein the head of the anchor is a solid construction.

23. The arrangement of claim 21, wherein the anchor is positionable in a first position at which the external drive structure of the anchor is engaged with the internal drive socket of the yoke, and a second position at which the external drive structure of the anchor is disengaged from the internal drive socket of the yoke.

24. The arrangement of claim 23, wherein the anchor and the yoke are in a fixed position relative to one another when the anchor is in the first position.

25. The arrangement of claim 23, wherein the anchor and the yoke are permitted to pivot relative to one another when the anchor is in the second position.

26. The arrangement of claim 21, wherein the fastener locks the yoke, the anchor, and a connecting rod received by the yoke in a fixed position relative to one another.

27. The arrangement of claim 21, wherein the torque can be transferred from the yoke to the anchor in the absence of the connecting rod in the yoke.

28. A spinal stabilization assembly comprising:
   an anchor having a spherical head and a shank extending from the spherical head, the spherical head of the anchor including an external drive structure comprising a plurality of external flat surfaces arranged around a periphery of the spherical head; and
   a retainer having a longitudinal axis, the retainer including a rod receiving region configured for receiving a connecting rod generally perpendicular to the longitudinal axis of the retainer and an anchor receiving region configured for receiving the spherical head of the anchor;
   wherein the anchor receiving region includes an internal drive structure comprising a plurality of internal flat surfaces; and
   wherein the spherical head of the anchor is positioned in the anchor receiving region such that the shank of the anchor is generally aligned with the longitudinal axis of the retainer and the plurality of external flat surfaces of the external drive structure of the spherical head of the anchor interface with the plurality of internal flat surfaces of the internal drive structure of the retainer.

29. The spinal stabilization assembly of claim 28, wherein the retainer is selectively pivotable relative to the anchor.

30. The spinal stabilization assembly of claim 28, wherein the retainer includes a first arm extending from a main body portion and a second am extending from the main body portion, wherein the first arm and the second am define the rod receiving region therebetween.

31. The spinal stabilization assembly of claim 30, further comprising:
   a connecting rod positioned in the rod receiving region such that the connecting rod extends generally perpendicular to the longitudinal axis of the retainer.

32. The spinal stabilization assembly of claim 31, further comprising:
   a securing member configured to secure the connecting rod in the rod receiving region, the securing member positioned between the first arm and the second am of the receiver.

33. The spinal stabilization assembly of claim 32, wherein the securing member is a threaded fastener threadedly engaged with a threaded portion of the first arm and a threaded portion of the second arm.

* * * * *